United States Patent [19]
Beck et al.

[11] 4,235,638
[45] Nov. 25, 1980

[54] SULFONATO-ORGANOSILANOL COMPOUNDS AND AQUEOUS SOLUTIONS

[75] Inventors: Boyd R. Beck, Spring City, Utah; Frank T. Sher; George V. D. Tiers, both of St. Paul, Minn.

[73] Assignee: Minnesota Mining and Manufacturing Company, St. Paul, Minn.

[21] Appl. No.: 895,528

[22] Filed: Apr. 11, 1978

[51] Int. Cl.$^3$ .......................... C09K 3/00; C07F 7/08
[52] U.S. Cl. ................................ 106/287.12; 556/428
[58] Field of Search ............................... 260/448.2 N; 106/287.12

[56] References Cited

U.S. PATENT DOCUMENTS

| | | | |
|---|---|---|---|
| 3,328,449 | 6/1967 | Haluska | 260/448.2 N |
| 3,412,129 | 11/1968 | Holdstock | 260/448.2 W |
| 3,507,897 | 4/1970 | Kanner et al. | 260/448.2 N |
| 3,513,183 | 5/1970 | Morehouse | 260/448.2 N |
| 3,531,507 | 9/1970 | Morehouse | 260/448.2 N |

*Primary Examiner*—Paul F. Shaver
*Attorney, Agent, or Firm*—Cruzan Alexander; Donald M. Sell; James V. Lilly

[57] ABSTRACT

Sulfonato-organosilanol compounds and aqueous solutions and compositions thereof are provided which have at least one sulfonato-organic substituent therein. The weight percentage of oxygen in the compounds is at least about 30% and the weight percentage of silicon in the compounds is not greater than about 15%, these percentages being taken with reference to the water-free acid form of the compounds. Hydrophilic siliceous surfaces and processes for imparting hydrophilicity to such surfaces are also provided.

38 Claims, No Drawings

SULFONATO-ORGANOSILANOL COMPOUNDS AND AQUEOUS SOLUTIONS

BACKGROUND OF THE INVENTION

This invention relates to materials useful in the treatment of siliceous surfaces. More particularly it relates to compounds, aqueous solutions and compositions which are useful in imparting durable hydrophilicity to siliceous surfaces.

Although various types of materials have been suggested for use in imparting hydrophilicity to various substrates, all of such previously suggested materials have been less than desirable for one reason or another. For example, some of the earliest suggested materials for such use were common anionic or non-ionic surfactants (e.g., triethanolammonium oleate, sodium lauryl sulfate, sodium dodecylbenzenesulfonate, polyoxyalkylene sorbitol). These surfactants have been described for use in either solid or aqueous solution form. However, the major disadvantage associated with the use of such common surfactants is that the hydrophilicity and antifogging properties imparted by such materials simply do not exhibit very good durability during use, (i.e., such materials are easily dissolved by water and removed from the surface). Consequently, in order for such materials to be effective they must be reapplied to the surface at frequent intervals.

Another type of surfactant which has been described for use in imparting hydrophilic properties is a terpolymer of dimethyl, silicone, polyethylene oxide, and polypropylene oxide. This type of surfactant, which is described, for example, in U.S. Pat. No. 3,337,351, suffers from the same drawbacks as discussed above, namely easy dissolution by water.

Still another type of surface active agent is described in U.S. Pat. No. 3,187,033. This type of material contains S-C bonded sulfo groups and displays physical and chemical properties similar to soaps. Thus, for example, these materials exhibit substantial surface tension lowering capabilities.

U.S. Pat. No. 3,507,897 describes siloxane surface active agents in aqueous media. These solutions preferably have a pH of from 5 to 8 so that the agents do not degrade. Additionally, these agents are said to exhibit excellent surface tension lowering capabilities.

U.S. Pat. No. 3,328,449 describes sulfopropylated, organofunctional silane and siloxane materials which are useful as detergents, ion exchange resins, wetting agents, anti-stat agents and polymerization catalysts for siloxanes. It is said that these materials may be provided in solution form and that suitable solvents include water. However, it is also said that such solvents must not react with the solute. There is no discussion therein of stable aqueous solutions of sulfonato-organosilanols or of siliceous surfaces rendered hydrophilic by treatment therewith.

U.S. Pat. No. 3,455,877 describes organosilicon epoxides wherein the epoxy group (or the radical containing the epoxy group) is attached to silicon by a Si-C linkage. These materials are said to be useful as emulsifiers, plasticizers, lubricants, etc. They are also said to be useful in preparing hydroxy sodium sulfonates by reacting the epoxides with sodium sulfite. There is no discussion of the preparation of stable aqueous solutions of such compounds or of the durably hydrophilic surfaces produced by contacting such compositions with siliceous surfaces.

The present invention provides compounds, aqueous solutions and compositions which are useful for imparting durable hydrophilicity to siliceous surfaces as well as the durably hydrophilic surfaces themselves. The hydrophilic treatments of the present invention are particularly useful where easy grease and wax removal is desired or required. Thus, for example, the treatments are useful on glass surfaces such as household windows, automobile windshields and windows, eyeglasses, and bathroom mirrors; glazed ceramic surfaces such as ceramic tile and ceramic bathroom fixtures; and silicon oxide treated polymeric and non-polymeric surfaces.

Siliceous surfaces treated in accordance with the present invention are not rendered grease or wax repellent (i.e., they are not made oleophobic). Consequently, greases and waxes may attach to the treated surfaces. However, the treated surfaces are rendered readily cleanable so that grease and wax may be removed therefrom by simple water rinsing alone although very light rubbing may also be helpful in some instances.

Because the present invention imparts durable hydrophilicity to siliceous surfaces, such surfaces may be readily cleaned even after having been repeatedly previously soiled or marked by grease or wax and then cleaned. Moreover, surfaces treated in accordance with the present invention are substantially easier to clean than are surfaces which have not been so treated.

Examples of greases and waxes which have been found to be readily removable from surfaces treated in accordance with the present invention are butter, margarine, lard, natural sebum (skin oil), artificial sebum, motor oils, motor greases, paraffin wax and wax pencil marks. Still other substances such as elastomeric-based adhesives, pressure-sensitive adhesives, thermoplastic (solvent soluble) adhesives, thermosetting adhesives, epoxy adhesives, silicon based adhesives, etc. are readily removed from these surfaces.

Preferably the sulfonato-organosilanol compounds are provided in aqueous solutions. Surprisingly, such solutions are stable over long periods of time even at relatively high concentrations of the sulfonato-organosilanol compounds (e.g., 10% to 15% by weight). Thus, the treatment activity of the solutions is retained and no precipitate is formed therein upon prolonged storage. Moreover, such solutions may be provided at various concentrations of the sulfonato-organosilanol compounds. Consequently, the solutions may be provided in a concentrated form for storage or shipping that may be later diluted for use.

Additionally the preferred aqueous solutions provide thin, durable antifogging coatings on siliceous surfaces. Thus individual water droplets will not form and remain on surfaces treated with said solutions (i.e., said surfaces do not fog over) despite repeated exposures to conditions of high humidity.

Surprisingly the foregoing results are achieved even though the sulfonato-organosilanol compounds do not exhibit typical surfactant characteristics. Thus these compounds do not significantly affect the surface tension of aqueous media.

SUMMARY OF THE INVENTION

In accordance with the present invention there are provided novel sulfonato-organosilicon compounds (sometimes referred to hereinafter as sulfonato-silanols) having at least one sulfonato-organic substituent, wherein the weight percentage of oxygen in the compound is at least about 30%, and wherein the weight percentage of silicon in the compound is not greater than about 15%, said percentages being taken with reference to the water-free acid form of the compound. As it is used herein, the acid form of the silanol compound refers to a compound which has a sulfonato substituent of the formula —SO$_3^-$H$^+$. All percentage determinations with respect to oxygen and silicon are calculated relative to this form whether or not the compound under discussion is itself the acid form or is present in an aqueous solvent and/or as a salt of the acid.

Two types of novel sulfonato-silanols are provided. They are the organosilanol-sulfonic acids and the organosilanolate-sulfonic acid salts (each of which are described more fully hereinafter).

Also provided herein are novel aqueous solutions and compositions of the sulfonato-organosilanol compounds. These aqueous solutions include solutions of the novel organosilanol-sulfonic acids and organosilanolate-sulfonic acid salts in addition to solutions of the known organosilanol-sulfonic acid salts. As it is used herein, the term "aqueous solutions and compositions" refers to solutions and compositions wherein water is present. Such solutions and compositions may employ water as the only solvent or they may employ combinations of water and organic solvents such as alcohol and acetone. Moreover substantial amounts of the organic solvents may be included in the combinations.

Still further provided are articles comprising a siliceous surface having a durably hydrophilic organic layer bound thereto. Also provided is a process for rendering siliceous surfaces durably hydrophilic.

DETAILED DESCRIPTION OF THE INVENTION

The sulfonato-organosilanol compounds of the invention may be prepared by converting the corresponding precursor organic silane to the organosilanolate or the organosilanol-sulfonic acid salt followed by subsequent conversion to the desired product.

Precursor silane materials which are useful in preparing the compounds and solutions of the present invention have a reactive functional group on the organic group and from one to three hydrolyzable groups on the silicon atom. An example of one useful type of precursor silane is one bearing an epoxide group on the organic group. This material may be converted to the organosilanolate-sulfonic acid salt by reacting an alcohol or water solution thereof with an aqueous solution of an alkali sulfite. The silanolate salt may be converted to the organosilanol-sulfonic acid by passing the silanolate solution through an acidic ion exchange resin such as "Amberlite IR-120" (acid form) available from Rohm and Haas Company. Both the silanolate salt and the sulfonic acid may be converted to the neutral pH organosilanol-sulfonic acid salt by neutralizing them with, for example, by neutralizing with the acid form.

An example of another type of useful precursor silane is one having ethylenic unsaturation in the organic group. This type of material may be converted to the organosilanol-sulfonic acid salt by reacting an alcohol solution thereof with an aqueous solution of an alkali bisulfite. The resultant sulfonic acid salt may be converted to the corresponding organosilanol-sulfonic acid by passing the silanol-sulfonic acid salt solution through an acidic ion exchange resin. Alternatively, the organosilanol-sulfonic acid salt may be converted to the organosilanolate-sulfonic acid salt by treating the organosilanol-sulfonic acid salt solution with an appropriate base.

Yet another example of a useful type of precursor silane is one bearing a thiol (i.e., mercapto) group on the organic group. This material may be converted to the corresponding organosilanol-sulfonic acid salt by oxidizing a solution of the precursor silane in acetone with an aqueous solution of potassium permanganate. The resultant silanol-sulfonic acid salt may then be converted to the corresponding organosilanol-sulfonic acid by passing the salt solution through an acidic ion exchange resin. Alternatively, the silanol-sulfonic acid salt may be converted to the corresponding organosilanolate-sulfonic acid salt by reacting it with an appropriate base.

The sulfonato-organosilanol compounds used in the solutions and compositions of the present invention have the formula

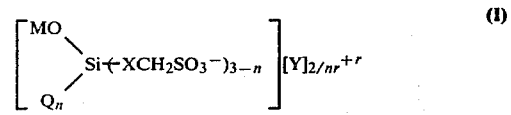

wherein
Q is selected from hydroxyl, alkyl groups containing from 1 to about 4 carbon atoms and alkoxy groups containing from 1 to about 4 carbon atoms;
M is selected from hydrogen, alkali metals and organic cations of strong organic bases having an average molecular weight of less than about 150 and a pK$_a$ of greater than about 11;
X is an organic linking group;
Y is selected from hydrogen, alkaline earth metals, (e.g., magnesium, calcium, etc.) organic cations of protonated weak bases having an average molecular weight of less than about 200 and a pK$_a$ of less than about 11 (e.g., 4-aminopyridine, 2-methoxyethylamine, benzylamine, 2,4-dimethylimidazole, 3-[2-ethoxy(2-ethoxyethoxy)]propylamine), alkali metals and organic cations of strong organic bases having an average molecular weight of less than about 150 and a pK$_a$ of greater than about 11 (e.g., $^+$N(CH$_3$)$_4$, $^+$N(CH$_2$CH$_3$)$_4$), provided that M is hydrogen when Y is selected from hydrogen, alkaline earth metals and organic cations of said protonated weak bases;
r is equal to the valence of Y; and
n is 1 or 2.

The weight percentage of oxygen in these compounds is at least about 30%, and preferably at least about 40%. Most preferably it is in the range of about 45% to 55%. The weight percentage of silicon in these compounds is no greater than about 15%. Each of these percentages is based on the weight of the compound in the water-free acid form.

The organic linking group X, is preferably selected from alkylene groups, cycloalkylene groups, alkyl-substituted cycloalkylene groups, hydroxy-substituted alkylene groups, hydroxy-substituted mono-oxa alkylene groups, divalent hydrocarbon groups having mono-oxa backbone substitution, divalent hydrocarbon groups having mono-thia backbone substitution, divalent hydrocarbon groups having monooxo-thia backbone substitution, divalent hydrocarbon groups having dioxo-thia backbone substitution, arylene groups, arylalkylene groups, alkylarylene groups and substituted alkylarylene groups. Most preferably X is selected from alkylene groups, hydroxy-substituted alkylene groups and hydroxy-substituted mono-oxa alkylene groups.

The organosilanol-sulfonic acids represent one class of novel compounds within the purview of formula I. These compounds have the formula

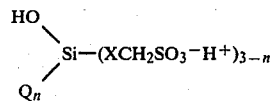
(II)

wherein Q, X and n are each as described above. Examples of organosilanol-sulfonic acids of formula II are $(HO)_3-Si-X-CH_2SO_3^-H^+$ (IIA)

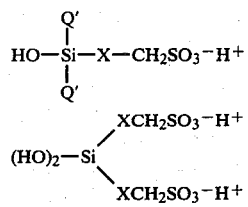
(IIB)

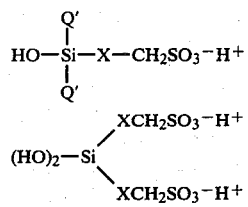
(IIC)

In these formulae X is as described above and Q' is an alkyl group which contains from 1 to about 4 carbon atoms. Representative compounds of formulae IIA, IIB and IIC include:

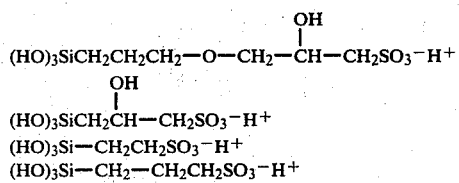
(a)

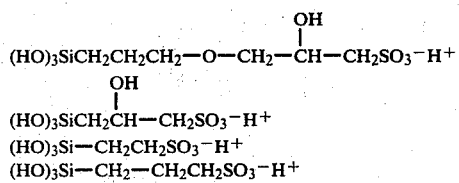
(b)

$(HO)_3Si-CH_2CH_2SO_3^-H^+$ (c)
$(HO)_3Si-CH_2-CH_2CH_2SO_3^-H^+$ (d)

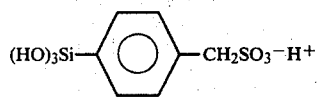
(e)

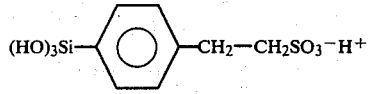
(f)

$(HO)_3SiCH_2CH_2CH_2-S-CH_2CH_2CH_2SO_3^-H^+$ (g)

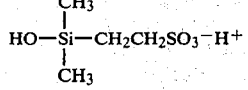
(h)

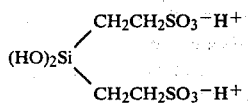
(i)

Of these specific compounds, those of formulae (a), (c), (d) and (i) are preferred. Compound (d) is a particularly preferred compound.

Useful starting materials in the preparation of compounds (a) through (i) above are respectively as follows:

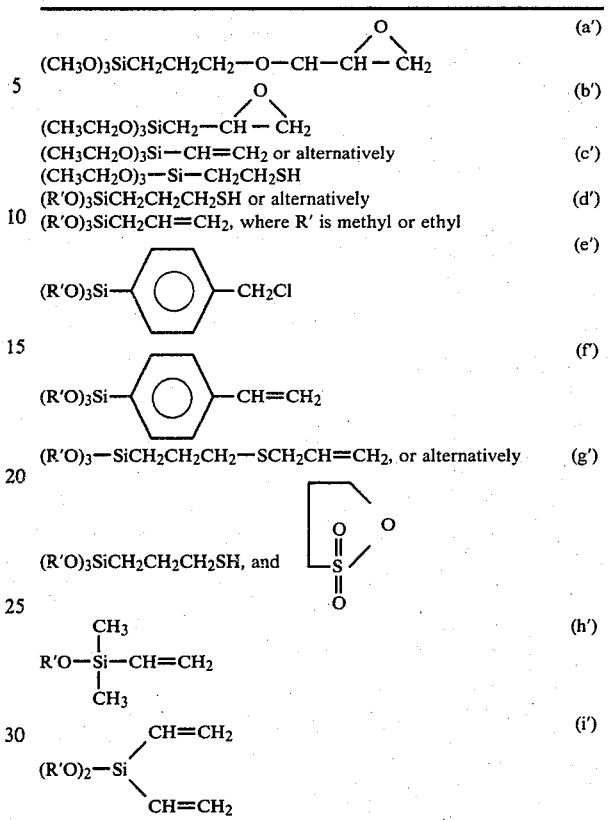

The aqueous solutions of the organosilanol-sulfonic acids are acidic. Thus they have a pH of less than about 5. Preferably they have a pH of less than about 3. Most preferably they have a pH in the range of about 0.5–2.5.

The organosilanolate-sulfonic acid salts represent another class of novel compounds within the purview of formula I. These compounds have the formula

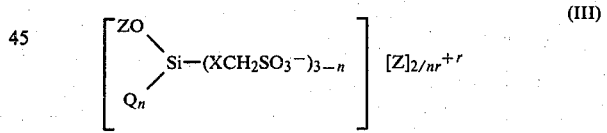
(III)

wherein Q, X, n and r are each as defined above, and wherein Z is selected from alkali metals and organic cations of strong organic bases having an average molecular weight of less than about 150 and a $pK_a$ of greater than about 11. Examples of organosilanolate-sulfonic acid salts of formula III are

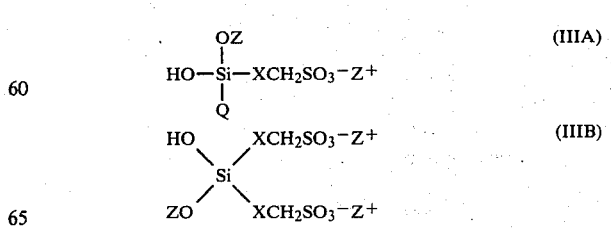
(IIIA)

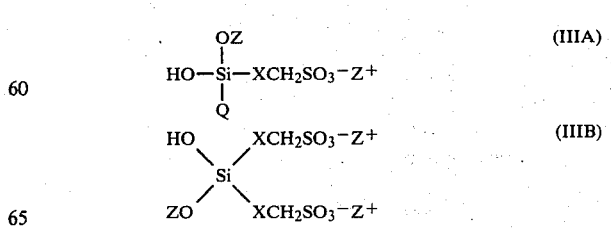
(IIIB)

Representative compounds of formulae IIIA and IIIB include:

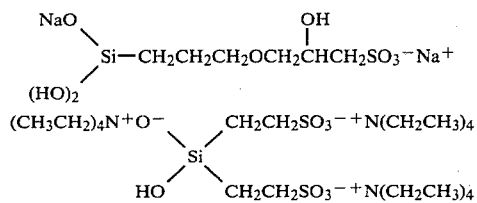

(a)

(b)

The aqueous solutions of the organosilanolate-sulfonic acid salts are basic. Thus they have a pH of greater than about 9. Preferably they have a pH of greater than about 10. Most preferably they have a pH in the range of about 11-13.

The known organosilanol-sulfonic acid salts represent yet another class of compounds within the purview of formula I which are useful in the aqueous solutions and compositions of the present invention. These compounds have the formula

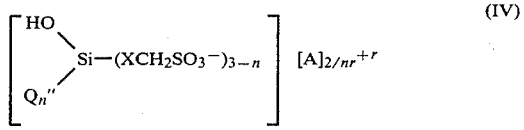

(IV)

wherein X, n and r are each as described above, Q" is selected from hydroxyl and alkyl groups containing from 1 to about 4 carbon atoms and A is selected from alkaline earth metals, organic cations or protonated weak bases having an average molecular weight of less than about 200 and a $pK_a$ of less than about 11, alkali metals and organic cations of strong organic bases having an average molecular weight of less than about 150 and a $pK_a$ of greater than about 11. Examples of organosilanol-sulfonic acid salts of formula IV are $(HO)_3—Si—XCH_2SO_3^-A^+$ (IVA)

$(HO)_2—Si—(XCH_2SO_3^-A^+)_2$ (IVB)

Representative compounds of formula IVA and IVB include:

 (a)

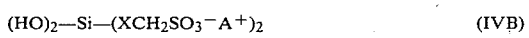 (b)

The aqueous solutions of the organosilanol-sulfonic acid salts are neutral. Thus they have a pH in the range of about 5 to 9. Preferably they have a pH in the range of about 6 to 8.

The aqueous solutions of the present invention may be used to impart hydrophilicity to a wide variety of substrates having siliceous surfaces with closely adjacent SiOH sites. Examples of such surfaces include window glass, mirror glass, borosilicate glass, lead glass, fused silica, soda glass, glazed ceramics and ceramic tiles, ceramic electrical insulations, decorative ceramics, porcelain ware, china ware, bone china, natural quartz, granite, feldspar, beryl, obsidian, enamelled iron and agate. Additionally polymeric and non-polymeric surfaces which have been vapor coated with a silicon oxide of the formula $-\!(SiO_2)\!-$ where x is 1 to 2 often termed "silicon monoxide" may be rendered hydrophilic in accordance with the present invention. Examples of polymeric surfaces which may be treated with silicon oxide and then rendered hydrophilic are polyester, polycarbonate, polyvinylchloride, polyvinylfluoride, polyvinylidene fluoride, polyimide, phenolic resin, polyethylene, nylon, polystyrene, polypropylene, cellulose acetate butyrate, polymethylmethacrylate, etc. Examples of non-polymeric surfaces which may be treated with said silicon oxide and then rendered hydrophilic are mica, aluminum, steel, painted surfaces, etc.

Preferably, the solutions used to treat the siliceous surfaces have a concentration of the appropriate sulfonato-silanol compounds of approximately 1% to 3% by weight. Lower or higher concentrations of the sulfonato-silanols may also be used (e.g., 0.1% to 30% or higher) if desired.

Siliceous surfaces may be easily rendered durably hydrophilic in accordance with the present invention. Thus, an aqueous solution of a sulfonato-organosilanol compound is applied to said surface under mild conditions (e.g., 10° C. to 60° C. at atmospheric pressure) followed by simple drying at room temperature (e.g., 23° C.) to obtain the hydrophilic properties. No catalyst or curative is needed in order to obtain these properties.

The hydrophilic treatment composition may be applied directly to the siliceous surfaces, especially to the silicon oxide treated polymeric and non-polymeric surfaces. However, it is preferred that the glass and glazed ceramic surfaces to be treated be freshly cleaned and activated either immediately prior to, or simultaneously with, the application of the aqueous solution. It has been found that the amount of the sulfonato-organosilanol compound which bonds to these substrates tends to be reduced as the length of time between the cleaning-activation step and the treatment step is increased. Moreover, such a delay also tends to diminish the durability of the hydrophilic surface.

A variety of techniques may be employed to clean and activate the surface. For example an abrasive household cleanser containing fine silica particles such as Ajax ® or an abrasive polishing material such as silica, alumina, talc, quartz, cerium oxide, zirconium oxide etc. is utilized followed by rinsing and, usually, drying. The surface may also be cleaned and activated by contacting it with materials such as hydrofluoric acid, chromic sulfuric acid, sodium hydroxide solutions, etc. again followed by rinsing and usually drying.

The exact material used to clean and activate the surface is somewhat dependent upon the nature of the treatment solution employed. Thus it is preferred that an abrasive material such as Ajax ® be employed in cleaning and activating the surface when an acidic or neutral pH treatment solution is to be employed. When a basic treatment solution is to be employed it is preferred that an acidic material such as hydrofluoric acid be employed in cleaning and activating the surface.

Alternatively an abrasive or polishing material may be incorporated into the aqueous solution so that the surface to be rendered hydrophilic may be cleaned, activated and made hydrophilic in one step. In this case the surface may be buffed with a soft dry cloth or rinsed with water to remove the abrasive material after application of the aqueous solution and conditioning.

It is preferred that the treatment be dried for a period of time before the surface is soiled or rinsed. During this time the sulfonato-organosilanol compound interacts with the siliceous surface and forms a durable hydrophilic layer thereon. At this point the treated surface may be described as "conditioned". It is believed that the organosilicon hydrophilic layer is formed when the

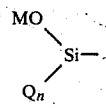

portion of the sulfonato-silanol reacts with available Si—OH sites on the siliceous surface to form Si—O—Si bonds thereon.

The treated surfaces are rendered effectively durably hydrophilic within a relatively short period of time after dryness has been obtained. For example, when aqueous solutions of the organosilanol-sulfonic acids are employed the surface may be rendered durably hydrophilic after as little as one minute of conditioning. However, typically about 15 minutes of conditioning time is preferred. When an organosilanolatesulfonic acid salt is employed the surface of the treated substrate is rendered durably hydrophilic after about 24 hours of conditioning. However, the degree of hydrophilicity tends to continue to improve over the first few days after treatment. When the organosilanol-sulfonic acid salt is employed the treated surface is rendered durably hydrophilic after about 2 hours of conditioning. The degree of hydrophilicity tends to continue to improve over the first few hours after treatment.

Although the compositions of the invention can be used to impart a high degree of hydrophilicity to a surface, it is also possible to convert the resulting hydrophilic surface to a hydrophobic surface by means of ion exchange. That is, the hydrophilic surface may be rinsed or otherwise contacted with certain cationic surfactants, quaternary fatty amines, etc., so that the sulfonato-organosilanol compound bonded to the surface of the substrate is converted to a salt of an organic cation bearing a hydrophobic tail. The process is totally reversible and accordingly, the surface may be converted back to a very hydrophilic state again (e.g., by treatment with aqueous alkali salt solutions) as desired.

The aqueous solutions of the present invention may be provided in the form of compositions having a variety of viscosities. Thus, for example, the viscosity may vary from a water thinness to a paste-like heaviness. They may also be provided in the form of gels. Additionally, a variety of other ingredients may be incorporated in the aqueous solutions. Thus, for example, abrasive materials (or polishing agents), conventional anionic surfactants and detergents and suspending aids or thickening agents may be included therein.

The abrasive materials or polishing agents may have a variety of particle sizes. However, it is preferred that they not be so large as to visibly abrade the surface which is treated. These materials may comprise up to about 60% by weight of the composition. Preferably they comprise from about 5% to 10% by weight of the composition. The exact abrasive material selected is dependent upon the acidity of the aqueous solution. Thus acidic abrasive materials are employed when acidic treatment solutions (i.e., solutions of organosilanol-sulfonic acids) are employed. Basic abrasive materials are employed when basic treatment solutions (i.e., solutions of organosilanolate-sulfonic acid salts) are employed. Acidic or basic abrasive materials may be employed when neutral treatment solutions (i.e., solutions of organosilanol-sulfonic acid salts) are employed. Representative examples of useful abrasive materials or polishing agents include amorphous silica (e.g., "Imsil" A-10, A-15 and A-25, commercialy available from Illinois Mineral Company), calcium carbonate, talc, silicon carbide, α-quartz, alumina, zirconium oxide, cerium oxide, etc.

The anionic surfactants and detergents included in the aqueous solutions and compositions of the invention typically comprise up to about 5% by weight of the composition. Preferably they comprise from about 0.1 to 1% by weight of the composition. More or less of the surfactants or detergents may be utilized if desired. Representative examples of useful surfactants or detergents include sodium dodecylbenzenesulfonate ("Siponate" DS-10 available from Alcolac Incorporated), sodium dodecyldiphenyloxidedisulfonate ("Dowfac" 2Al available from Dow Chemical Company), sodium dodecyl sulfate, $C_8F_{17}SO_3H$, sodium dioctylsulfosuccinate, (Aerosol ® OT, available from American Cyanamid Company), sodium heptadecyl sulfate (Tergitol ® Anionic 7, commercially available from Union Carbide Corporation).

The suspending or thickening aids which may be employed in compositions of the present invention must be compatible with the aqueous solutions of the invention. Thus the thickening aids must maintain the abrasive material (described hereinbefore) in an easily redispersible state for an extended period of time (e.g., 12 months or more). Thus useful thickening aids prevent the formation of a hard cake of abrasive material. Additionally the suspending or thickening aids are chemically stable in the aqueous composition. That is they do not degrade therein or adversely affect the performance of the composition.

The suspending or thickening aids typically comprise up to about 5% by weight of the composition. Preferably they comprise from about 0.1% to 1% by weight of the composition. However, more or less of such aids may be employed if desired. Representative examples of useful thickening or suspending aids include magnesium aluminum silicates such as "Veegum" HV, K and T available from R. T. Vanderbilt Company, "Gel White" GT and "Mineral Colloid MO" available from Georgia Kaolin Company, and "Ben-A-Gel" available from National Lead Industries. Other useful suspending or thickening aids include fumed silica such as Cab-O-Sil ® M-5 available from Cabot Corporation and xanthan gums such as "Keltrol" available from Kelco Corporation.

Solvents may also be included in the hydrophilic treatment solutions and compositions so as to improve their freeze-thaw stability. Typically the solvents comprise up to about 40% by weight of the compositions and preferably in the range of about 5–10% by weight of the compositions. Representative examples of useful solvents include the lower alcohols such as methanol, ethanol, propanol, 2-propanol, etc. A variety of other solvents might also be used as will be apparent from this specification.

The hydrophilic layer obtained by the treatment described hereinbefore is transparent, haze-free, thin and durable. Thus, for example, a cleaned and activated glass surface which has been treated with an aqueous solution of the present invention possesses optical qualities comparable to those of a non-treated but cleaned glass surface. That is, both the reflectance and transmission of the treated glass surface are essentially identical to those of the untreated glas surface.

Moreover, these hydrophilic layers are extremely thin, being less than abut 100 nanometers thick. The thinness of the layers may be shown by a variety of techniques such as X-ray Photoelectron Spectroscopy (ESCA), Ion Scattering Spectroscopy (ISS), Secondary Ion Mass Spectrometery (SIMS), radiolabeled $^{35}$S and ellipsometry. These techniques indicate that the hydrophilic layer is less than 100 nanometers thick and, often corresponds to a thinness calculated to be in the range of 1 to 2 molecular layers of the sulfonato-organosilanol compound used in the aqueous treatment solution.

A variety of techniques may be employed to demonstrate the durability of the hydrophilic treatment. These techniques include the use of radiolabelled $^{35}$S, a Cationic Dye Exchange test and a "Spreading Water Drop" test. Typically these tests are employed in conjunction with a "Cyclic Wear" test. These techniques are now described in more detail.

RADIOLABELLED $^{35}$S TEST

Radioactive $^{35}$S in an alkali sulfite is used to prepare an aqueous solution of the desired sulfonato-organosilanol compound. This solution is applied to a freshly cleaned and activated siliceous surface and allowed to condition thereon. The treated surface is then rinsed with deionized water to remove any non-bonded radiolabelled sulfonato-organosilanol compound. The radioactivity of the treated surface is then determined by means of a flow-counter gas ionization system (available as Model 186 from Nuclear Chicago Corporation).

CATIONIC DYE EXCHANGE TEST

A section of a siliceous surface to be tested is contacted with an excess of a 0.01 molar solution (pH of 4) of a cationic dye (U.S.P. methylene blue (chloride) dye) in deionized water. The dye solution is allowed to dry thereon and bind to the surface of the section. The section is then rinsed with deionized water to remove any unbound dye, the remaining bound dye is then removed from the surface by carefully rinsing it with 3 ml of a 0.5% by weight solution of the potassium salt of perfluoro(ethylcyclohexane) sulfonic acid in absolute ethanol. The rinse solution is collected and the dye concentration therein determined by measuring the spectrophotometric absorbance thereof in a 10 mm cell at a wavelength of 655 nanometers (nm). A high absorbance in the rinse solution indicates that there is a high level of sulfanato-organosilicon compound on the surface of the section. Direct densitometry may also be utilized to measure dye binding.

Siliceous substrates treated in accordance with the present invention bind at least about 50% (and preferably at least about 100%) by weight more of the methylene blue dye expressed as the chloride than do the respective normal siliceous surfaces. Normal siliceous surfaces are those which are clean and equilibrated and free of hydrophilic treatments and other foreign matter. Normal surfaces may be prepared by a process of normalization wherein the surface has been cleaned and activated and then allowed to equilibrate over a 24 hour period in an ambient atmosphere at room temperature. The cleaning and activating may involve abrasive polishing, treating with acidic or basic solutions, or flame (heat) treatment followed by rinsing with deionized water and careful drying at ambient (e.g., 23° C.) temperature. For example, normalization may be achieved by (i) soaking the treated surface in a chromic/sulfuric acid cleaning solution at about 23° C. for 16 hours, (ii) rinsing it with deionized water and (iii) air drying it at about 23° C. for 24 hours. This latter treatment is especially suited for removing existing hydrophilic organic layers to permit comparision measurements of normalized siliceous substrates.

SPREADING WATER DROP TEST

A section of a siliceous surface to be tested is either cleaned and activated with an aqueous slurry of an abrasive material or cleaned, activated and rendered hydrophilic according to the invention. The hydrophilically treated surface is allowed to condition for the desired time. A one microliter (1.0 μl) drop of deionized water is placed on the appropriate horizontally oriented siliceous surface. The area covered by the drop of water is then determined. An area of coverage of less than about 10 mm$^2$ is indicative of a nonhydrophiic surface while an area of coverage of more than about 10 mm$^2$ or more is indicative of a hydrophilic surface (i.e., one exhibiting grease and wax release). As the degree of hydrophilicity of the treated surface increases the area of coverage also increases. Thus an area of 12 mm$^2$ or more is indicative of a hydrophilic surface having easy grease and wax release while an area of 15 mm$^2$ or more is indicative of a surface having good anti-fogging characteristics.

CYCLIC WEAR TEST

A surface to be tested is placed in a Gardner Straight Line Washability and Abrasion Machine. A pad of wet cheesecloth under a pressure of about 4 kilopascals is placed over the surface and passed back and forth repeatedly thereover. Each cycle equals one back and forth pass of the cheesecloth pad.

The foregoing invention is further illustrated by means of the following examples:

EXAMPLE 1

An organosilanolate-sulfonic acid salt having the formula

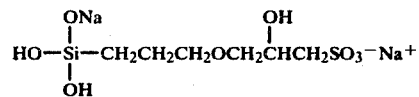

was prepared. A solution comprising 0.5 gram (g) gammaglycidoxypropyltrimethoxy silane and 2.5 g methanol was added slowly to a solution of 0.27 g sodium sulfite (Na$_2$SO$_3$) and 5 g water. The reaction mixture was stirred at 50° C. for 16 hours and then diluted with water to 3% by weight solids. A small amount of a surfactant (0.5% by weight sodium dodecylbenzenesulfonate) was added to the diluted reaction mixture and agitated therewith until uniform to provide a basic hydrophilic treatment solution having a pH of 12.8.

EXAMPLE 2

An organosilanol-sulfonic acid having the formula

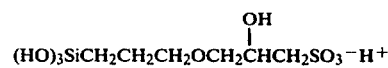

was prepared. An 8% by weight solution of the organosilanolate-sulfonic acid salt of Example 1 in a methanol/water mixture (2/1 by volume) was passed through an excess of the acid form of Amberlite ®

IR-120 (an ion exchange resin commercially available from Rohm and Haas Company). This provided an acid treatment solution having a pH of 1.6. The solution was diluted to 2% solids by weight with deionized water and 0.5% by weight sodium dodecylbenzenesulfonate was added thereto to provide the final hydrophilic treatment solution.

EXAMPLE 3

An organosilanol-sulfonic acid having the formula $(HO)_3SiCH_2CH_2SO_3^-H^+$ was prepared. A solution of 83.6 g triethoxyvinylsilane and 1440 milliliters (ml) absolute ethanol was added slowly to a solution of 100 g sodium bisulfite, 10 g sodium nitrate, 10 g sodium nitrite and 2200 ml of water. This reaction mixture was stirred at about 23° C. for three days. The mixture was then passed through approximately 800 g Amberlite ® IR-120 (acid form) ion exchange resin. The pH of the final solution was observed to be about 1. About 0.5% by weight dodecylbenzenesulfonic acid was then added to the reaction mixture and dissolved therein to provide an acidic hydrophilic treatment solution.

EXAMPLE 4

An organosilanol-sulfonic acid salt having the formula $(HO)_3SiCH_2CH_2SO_3^-K^+$ was prepared. A solution comprising 0.51 g (2 mmol) 2-mercaptoethyltriethoxysilane and 4 ml acetone was added with stirring over a five minute period to an ice-bath cooled solution of 1.26 g (8 mmol) potassium permanganate and 8 ml distilled water. The ice-bath was removed and stirring was continued for two hours. About 0.3% by weight sodium dodecylbenzenesulfonate was then dissolved in the reaction mixture. The mixture was then filtered to give a pale yellow neutral hydrophilic treatment solution which had a pH of about 8.

A portion of the solution was evaporated to recover the salt. The structure of the salt was confirmed by nuclear magnetic resonance spectra (nmr).

EXAMPLE 5

An organosilanol-sulfonic acid having the formula $(HO)_3SiCH_2CH_2CH_2SO_3^-H^+$ was prepared. A solution of 1.96 g (0.01 moles) gamma-mercaptopropyltrimethoxysilane and 20 ml acetone was added rapidly to a solution of 3.16 g (0.02 moles) potassium permanganate and 60 ml of water. The resulting mixture turned brown and immediately warmed and increased in pH to approximately 9. The mixture was filtered and the precipitated $MnO_2$ washed with deionized water (300 ml). Approximately 2 g of dried $MnO_2$ was recovered. The filtrate was ion exchanged as described in Example 2 to provide an acidic hydrophilic treatment solution.

A portion of the product was recovered and titrated to determine the yield of sulfonic acid therein. The yield was calculated to be 86.8% on the basis of the titration.

Alternative procedures for preparing the organosilanol-sulfonic acid of this example are possible. Thus the acid was also made by adding a solution of 4.4 g (22.4 mmol) gamma-mercaptopropyltrimethoxysilane and 45 ml of reagent acetone to an ice-bath cooled solution of 17.8 g (113 mmol) potassium permanganate and 90 ml distilled water with stirring over a five minute period. After the addition was complete the ice-bath was replaced by a cold water bath and stirring was continued at 23° C. until all the permanganate had been consumed (about two hours). The neutral pH mixture was filtered and ion-exchanged with Amberlite ® IR-120 (acid form) ion exchange resin to give an acidic treatment solution. The structure of the acid was confirmed by nmr. A small amount of a surfactant (i.e., 0.1–0.5% by weight sodium dodecylbenzenesulfonate) may be added to the solution.

The organosilanol-sulfonic acid of this example was also prepared by slowly adding a solution of 2.04 g (10 mmol) allyltriethoxysilane and 35 ml absolute ethanol to a stirred solution of 2.08 g (20 mmol) sodium bisulfite, 0.2 g (2.9 mmol) sodium nitrite, 0.2 g (2.35 mmol) sodium nitrate and 50 ml of distilled water. Stirring was continued at room temperature for 96 hours. The resulting product was rendered acidic by ion exchange as described in Example 2. Analysis by nmr confirmed the structure.

EXAMPLE 6

An organosilanol-sulfonic acid having the formula $(HO)_3SiCH_2CH_2CH_2SCH_2CH_2CH_2SO_3^-H^+$ was prepared. Solid $(CH_3O)_3SiCH_2CH_2CH_2SCH_2CH_2CH_2SO_3Na$ was prepared according to Example 1 of U.S. Patent No. 3,508,959. This compound was reacted with and dissolved in water. The resulting product was ion exchanged as described in Example 2 to give an acidic treatment solution.

EXAMPLE 7

An organosilanol-sulfonic acid having the formula $(HO)_2Si(CH_2CH_2SO_3^-H^+)_2$ was prepared. A solution comprising 8.6 g (0.05 mol) divinyldiethoxysilane and 200 ml absolute ethanol was slowly added dropwise to a stirred solution comprising 15.6 g (0.15 mol) sodium bisulfite, 1.56 g (18.4 mmol) sodium nitrate, 1.56 g (22.6 mmol) sodium nitrite and 300 ml distilled water. Stirring was continued at room temperature for 72 hours after which the solution was ion exchanged as described in Example 2 to give an acidic hydrophilic treatment solution. About 0.5% by weight sodium dodecylbenzene-sulfonate was added to the solution.

Prior to ion exchange, a portion of the sodium salt solution was examined using nmr and infrared (IR) analysis. Both confirmed the structure of the salt.

EXAMPLE 8

An organosilanol-sulfonic acid having the formula

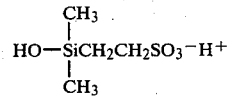

was prepared. A solution of 2.6 g (20 mmol) dimethylvinyl ethoxysilane and 66 ml absolute ethanol was added dropwise to a stirred solution of 4.54 g (43.6 mmol) sodium bisulfite, 0.45 g (5.3 mmol) sodium nitrate, 0.45 g (6.5 mmol) sodium nitrite and 100 ml of distilled water. Stirring was continued at room temperature for 96 hours to form the sodium salt of the sulfonic acid. The solution of the salt was ion exchanged as described in Example 2 to give an acid hydrophilic treatment solution. About 0.5% by weight sodium dodecylbenzenesulfonate was dissolved in the solution.

Prior to ion exchange, a portion of the solution was examined by nmr and IR techniques. These tests confirmed the above salt structure. The calculations also showed that the water-free acid form of the organosilanol-sulfonic acid was 15.2% silicon and 34.7% oxygen by weight.

EXAMPLE 9

An organosilanol-sulfonic acid having the formula

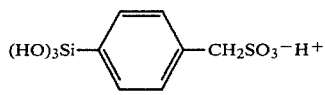

was prepared. A solution of 2.5 g (10 mmol) p-chloromethylphenyltrimethoxysilane and 25 ml absolute ethanol was slowly added dropwise to a stirred solution of 1.26 g (10 mmol) sodium sulfite and 30 ml distilled water. The mixture was stirred in a 75° C. oil bath for two hours and then at room temperature overnight to produce the sodium salt. The solution was then ion exchanged as described in Example 2 to give an acidic treatment solution. About 0.5% by weight sodium dodecylbenzenesulfonate was dissolved in the solution. The structure of the acid form was confirmed by nmr and IR techniques.

EXAMPLES 10-21

Thin coatings of the treatment solutions of Examples 1-9 were applied to separate glass and glazed ceramic substrates. In each case the substrates were cleaned and activated by scouring with a slurry of water and an abrasive household cleanser (e.g., Ajax ®) followed by water rinsing and drying with a soft dry cloth before application of the treatment solution. A clean cellulosic pad (e.g., a Colitho ® plate wipe) was used to immediately apply the treatment solutions as a thin visibly damp film. The resulting coatings were conditioned at room temperature and then tested for hydrophilicity by determining the ease with which substances such as butter, sebum (skin oil), artificial sebum, wax pencil marks and paraffin wax were removed from the treated surfaces. The treatment compositions and the conditioning times employed are set forth in Table 1. In each example both a glass and a glazed ceraic surface was tested.

TABLE 1

| EXAMPLE | TREATMENT COMPOSITION | CONDITIONING TIME |
|---|---|---|
| 10 | Ex. 1 | 3 Days |
| 11 | Ex. 2 | 3 Hours |
| 12 | Ex. 2 | 15 Min. |
| 13 | Ex. 3 | 3 Min. |
| 14 | Ex. 4 | 2 Hours |
| 15 | Ex. 5 (1st Process) | 5 Min. |
| 16 | Ex. 6 | 3 Hours |
| 17 | Ex. 7 | 2 Min. |
| 18 | Ex. 8 | 1 Hour |
| 19 | Ex. 8 | 2 Hour |
| 20 | Ex. 8 | 15 Min. |
| 21 | Ex. 9 | 2 Hour |

Each of the compositions provided durable hydrophilic treatments on both the glass and glazed ceramic surfaces. Moreover, each of the treatments allowed easy removal of the above-described substances by simply rinsing the treated surface with cold water. However, the substances were not removed from the untreated glass or glazed ceramic surfaces by simple rinsing with cold water.

EXAMPLE 22

The durable hydrophilicity of glass and glazed ceramic surfaces treated according to the invention was demonstrated. The glass and glazed ceramic surfaces were cleaned and activated as described in Examples 10-21 and then immediately made hydrophilic by applying a thin layer of the organosilanolatesulfonic acid salt treatment solution of Example 1 thereto with a Colitho ® plate wipe. The treated surfaces were conditioned for three days. When the Spreading Water Drop test was performed on the treated glass surface the drop covered an area of about 18 mm$^2$. When the Spreading Water Drop test was performed on an untreated glass surface the drop covered an area of only about 8 mm$^2$.

The treated surfaces were then tested for durability by marking them with a wax pencil (Reliance ® All-Surface Writer, White No. 3366); rinsing the surface with water from a wash bottle; and drying the surface with a soft dry towel. The cycle was repeated for a total of ten mark-wash challenges.

At all times the wax pencil provided a precise and legible mark on the dry surface which was easily rinsed off with water. There was no noticeable change in the ability of the wax pencil to mark the surface or in the ability of the water to wash away the mark over the course of the test.

The durability of these treatments was further demonstrated by showing the resistance of the treated glass surfaces to fogging. The surfaces were subjected to ten fogging cycles. Each cycle consisted of breathing on the treated glass surfaces; observing the presence or absence of fogging thereon; and then drying the surfaces by gentle wiping with a dry Colitho ® plate wipe. No fogging was observed after any of the cycles.

EXAMPLE 23

A glass microscope slide was cleaned and activated as described in Examples 10-21. A thin layer of the organosilanol-sulfonic acid treatment solution of Example 2 was immediately applied to one half of the slide. After conditioning for 15 minutes at 23° C. the slide was rinsed with tap water and wiped dry with a Colitho ® plate wipe. The resulting hydrophilic layer was thin, durable and optically transparent. A quantitative verification of the lack of optical impairment by the hydrophilic layer was provided by measuring the % transmittance and the % reflectance of the treated and untreated portions of the slide. A Gardner Hazemeter using a General Electric RP11 lamp with a Hunter Y green filter as a light source was used for the measurements. The transparency of the treated and untreated areas of the slide are set forth in Table 2. As can be seen from the data, the hydrophilic treatment caused no adverse effect upon the transparency of the glass slide.

TABLE 2

|  | AIR | TREATED GLASS | UNTREATED GLASS |
|---|---|---|---|
| % Transmittance | 100.0 | 92.0 | 92.0 |
| % Reflectance | 0.0 | 0.2 | 0.1 |

EXAMPLE 24

Example 2 was repeated except that radioactive ($^{35}$S) sodium sulfite (available from Amersham/Searle Corporation) was employed in place of non-radioactive sodium sulfite. The resultant aqueous treatment solution of radiolabelled organosilanol-sulfonic acid was applied to separate glass microscope slides which had been cleaned and activated as described in Examples 10–21. The slides were conditioned at 23° C. for 15 minutes. They were then subjected to 5 cycles in the Cyclic Wear test, rinsed with deionized water and air dried at 23° C.

The radioactivity of the thin, durable, transparent hydrophilic surface was quantitatively determined with a flow-counter gas ionization system (Model 186 from Nuclear-Chicago Corporation). From the data obtained it was determined that there were an average of 10.3 molecules of the organosilanol-sulfonic acid compound per square nanometer of surface area on the treated portion of the glass slide.

EXAMPLE 25

Two glass surfaces were cleaned and activated as described in Examples 10–21. The surfaces were made durably hydrophilic by immediately applying a thin layer of the organosilanol-sulfonic acid treatment solution of Example 2. One of the treated surfaces was conditioned for 3 hours at 23° C. while the other was conditioned for 15 minutes at 23° C.

The hydrophilicity of the treated surfaces was demonstrated by applying a section of Scotch ® Brand Magic Mending Tape and a section of No. 222 autoclave tape (commercially available from Minnesota Mining and Manufacturing Company) to each of the treated substrates. Initially, each of the tapes adhered well to the glass. However, when the treated surfaces were sprayed with, or immersed, in water the tapes each exhibited virtually no adherence to the surfaces. There was no noticeable difference in hydrophilicity based on conditioning time.

Additionally, adhesives such as Duco ® Cement (available from E. I. duPont deNemours Company), EC-847 (available from Minnesota Mining and Manufacturing Company), and Silastic 732-RTV (available from General Electric Company) were easily removed by simple water rinsing from the treated surfaces.

EXAMPLE 26

The durable hydrophilicity of the hydrophilic treatment of the invention was demonstrated by showing its resistance to repeated exposure to fogging conditions. One half of a bathroom mirror was cleaned and activated as described in Examples 10–21. This portion of the mirror was then immediately dried and treated with the organosilanol-sulfonic acid treatment solution of Example 2. The treated portion of the mirror resisted fogging in conditions of high humidity for at least six months while the untreated portion of the mirror repeatedly fogged in such conditions.

EXAMPLE 27

This Example demonstrates the reversible hydrophilicity of siliceous substrates treated in accordance with the present invention. Example 25 was repeated on a glass surface and with a conditioning time of 15 minutes at 23° C. The hydrophilic surface was then rendered hydrophobic by ion exchange by rinsing it with deionized water and then a 0.1% by weight solution of hexadecyltrimethylammonium chloride in deionized water. Then the surface was subsequently rendered hydrophilic by rinsing it with a 0.1% by weight solution of sodium chloride in deionized water to replace the quaternary ammonium cations with sodium cations. The nature of the surface can be changed from hydrophilic to hydrophobic to hydrophilic, etc. many times with no noticeable effect on the appropriate (i.e., hydrophilic or hydrophobic) nature thereof.

The hydrophilicity and hydrophobicity of the surface after each conversion was shown by the Spreading Water Drop test. After the surface had been rendered hydrophilic the water drop covered an area of at least 18 mm$^2$. After the surface had been rendered hydrophobic the water drop covered an area of less than 3 mm$^2$.

EXAMPLES 28–32

Several glass slides were cleaned and activated as described in Examples 10–21. One half of each slide was then immediately made durably hydrophilic by applying a thin layer of one of the aqueous treatment solutions according to the present invention. The slides were then tested for wettability and cleanability after exposure to an accelerated weathering test and an elevated temperature test. Separate slides were used for each test.

The accelerated weathering test was performed with a "Q-U-V" accelerated weathering instrument (available from the Q Panel Company). The instrument employed an eight hour cycle which consisted of a four hour exposure to ultraviolet light at 60° C. followed by a four hour condensation period at 50° C. The elevated temperature test was performed by placing the treated slides in sealed containers and placing the containers in ovens at 60° C. and 110° C.

Wettability of the treated and untreated portions of the slides was determined by the Spreading Water Drop Test. Cleanability was determined by measuring the ease with which a mark made by a wax pencil (Reliance ® All Surface Writer, White No. 3366) was removed by simple water rinsing. Failure was deemed to have occurred when either the wettability or cleanability of the treated portion of the slide was approximately equal to that of the untreated portion of the glass slide. The treatment compounds used and the results of the tests are set forth in Table 3. As can be seen from this data, the hydrophilic treatments of the present invention are very durable.

TABLE 3

| EX-AMPLE | TREATMENT COMPOSITION | ACCELERATED WEATHERING | HEAT EXPOSURE 60° C. | HEAT EXPOSURE 100° C. |
|---|---|---|---|---|
| 28 | (HO)$_3$SiCH$_2$CH$_2$CH$_2$OCH$_2$CH(OH)CH$_2$SO$_3^-$H$^+$ | 22 | 400 | 24 |
| 29 | (HO)$_3$SiCH$_2$CH$_2$CH$_2$SO$_3^-$H$^+$ | 81 | >2500 | >5000 |
| 30 | (HO$_3$)SiCH$_2$CH$_2$SO$_3^-$H$^+$ | 22 | 400 | >5000 |
| 31 | (HO)$_2$Si(CH$_2$CH$_2$SO$_3^-$H$^+$)$_2$ | 22 | 400 | >5000 |

Column header: TIME (HRS) TO OBSERVED FAILURE

TABLE 3-continued

| EXAMPLE | TREATMENT COMPOSITION | TIME (HRS) TO OBSERVED FAILURE | | |
|---|---|---|---|---|
| | | ACCELERATED WEATHERING | HEAT EXPOSURE 60° C. | 100° C. |
| 32 | HO—Si(CH$_3$)(CH$_3$)—CH$_2$CH$_2$SO$_3^-$H$^+$ | * | 400 | >5000 |

*Not measured

EXAMPLE 33

A portion of the organosilanolate-sulfonic acid salt treatment solution (3% by weight solids) of Example 1 was titrated with the organosilanol-sulfonic acid treatment solution (3% by weight solids) of Example 2 to form a final treatment solution with a pH of 7. Glass slides were cleaned and activated as described in Examples 10–21 and then immediately these slides were treated with the neutral treatment solution of this Example. The slides were conditioned for about 45 minutes at 23° C. The resultant treated surfaces were tested for wax and grease release and fog resistance as described in Example 22. They were found to be durably antifogging and repeatedly easily cleanable by water rinsing after being marked with a wax pencil.

Slides cleaned, activated and treated as described in this Example and then conditioned for two hours or longer at 23° C. also showed hydrophilic properties as shown by the "Spreading Water Drop" Test. Thus a 1.0 µl drop of deionized water placed on a treated horizontal surface covered 21.2 mm$^2$ while a 1.0 µl drop of water placed on an untreated horizontal surface covered less than about 8 mm$^2$.

EXAMPLES 34–59

Neutral and basic treatment solutions were prepared by titrating or neutralizing separate portions of treatment solutions prepared according to Examples 2 and 3 in water with lithium hydroxide, sodium hydroxide, potassium hydroxide, rubidium hydroxide, cesium hydroxide, magnesium carbonate, calcium carbonate, barium hydroxide, tetraethyl ammonium hydroxide, N-benzyltrimethylammonium hydroxide, tetramethyl guanidine and 3[2-ethoxy(2-ethoxyethoxy)] propylamine. The solutions were applied to a portion of separate glass slides which had been cleaned and activated as described in Examples 10–21 to provide durably hydrophilic surfaces thereon. The hydrophilicity of the treated surfaces was demonstrated by their wax release and antifogging characteristics. Wax release was measured by marking the surface with a wax pencil (Reliance® All Surface Writer, White No. 3366) and then rinsing the mark off with a stream of water from a wash bottle. The resultant wax release was rated on a scale of 0 to 5 with 0 indicating no significant release and 5 indicating complete release.

Antifogging was measured by breathing upon the treated surface and observing the ability of fog to form thereon. Antifogging was measured as "poor", "fair", "good", or "excellent". "Poor" indicates that one can detect very little difference in antifogging characteristics between the treated and untreated portions of the slide. "Fair" indicates that one can detect some minor areas of fogging on the treated portion of the slide. "Good" indicates that one can observe no fogging on the treated portion of the slide. "Excellent" indicates that one can observe no fogging on the treated portion and that Newton's rings may be seen when the moisture is drying after said treated portion has been breathed upon. The results of the tests are given in Table 4.

TABLE 4

| EX. | TREATMENT SOLUTION REFERENCE EX. | CATION | pH | CONDITION TIME | HYDROPHILICITY WAX RELEASE | ANTIFOGGING |
|---|---|---|---|---|---|---|
| 34 | Ex. 2 | Li$^+$ | 12.9 | 3 Days | 5 | Excellent |
| 35 | Ex. 2 | Rb$^+$ | 12.9 | 3 Days | 5 | Excellent |
| 36 | Ex. 2 | K$^+$ | 12.9 | 3 Days | 5 | Excellent |
| 37 | Ex. 2 | Et$_4$N$^+$ | 12.9 | 3 Days | 5 | Good |
| 38 | Ex. 2 | TMG$^+$ | 12.7 | 3 Days | 4 | Fair |
| 39 | Ex. 2 | Cs$^+$ | 7.0 | 2 Hours | 5 | Excellent |
| 40 | Ex. 2 | K$^+$ | 7.0 | 2 Hours | 5 | Excellent |
| 41 | Ex. 2 | Rb$^+$ | 7.0 | 2 Hours | 5 | Excellent |
| 42 | Ex. 2 | Et$_4$N$^+$ | 7.0 | 2 Hours | 4 | Fair |
| 43 | Ex. 2 | TMG$^+$ | 7.0 | 16 Hours | 4 | Poor |
| 44 | Ex. 2 | Li$^+$ | 7.0 | 2 Hours | 5 | Excellent |
| 45 | Ex. 2 | Mg$^{+2}$ | 7.6 | 16 Hours | 5 | Excellent |
| 46 | Ex. 2* | Ca$^{+2}$ | 6.8 | 16 Hours | 5 | Fair |
| 47 | Ex. 2* | Ba$^{+2}$ | 6.9 | 3 Hours | 4 | Poor |
| 48 | Ex. 2 | NBTM$^+$ | 12.5 | 3 Days | 4 | Fair |
| 49 | Ex. 2 | ETOP$^+$ | 10.2 | 3 Days | 4 | Poor |
| 50 | Ex. 3 | RB$^+$ | 12.7 | 3 Days | 5 | Excellent |
| 51 | Ex. 3 | Li$^+$ | 11.9 | 3 Days | 5 | Excellent |
| 52 | Ex. 3 | Cs$^+$ | 12.9 | 3 Days | 5 | Excellent |
| 53 | Ex. 3 | TMG$^+$ | 12.4 | 3 Days | 5 | Fair |
| 54 | Ex. 3 | Rb$^+$ | 7.0 | 2 Hours | 5 | Excellent |
| 55 | Ex. 3 | Li$^+$ | 7.0 | 2 Hours | 5 | Excellent |
| 56 | Ex. 3 | Cs$^+$ | 7.0 | 2 Hours | 4 | Excellent |
| 57 | Ex. 3 | TMG$^+$ | 7.0 | 2 Hours | 4 | Poor |
| 58 | Ex. 3 | Mg$^{+2}$ | 7.8 | 16 Hours | 5 | Excellent |
| 59 | Ex. 3 | Ca$^{+2}$ | 6.8 | 16 Hours | 5 | Fair |

Et$_4$N$^+$ = Tetraethylammonium
TMG$^+$ = Tetramethylguanidinium
NBTM$^+$ = N-benzyltrimethylammonium
ETOP$^+$ = 3 [-2-ethoxy(2-ethoxyethoxy)]propylammomium
*No surfactant used in treatment solution

EXAMPLES 60–64

One-part cleaner-treatment compositions were prepared which comprised 2% by weight of the organosilanol-sulfonic acid of Example 2, 10% by weight of abrasive material, 1% by weight of "Keltrol" thickener (a xanthan gum available from Kelco Corporation) and 87% by weight of diluent (82% water and 5% isopropyl alcohol).

About 0.5 g of each composition was applied to a separate piece of single strength window glass (7.6 centimeter by 7.6 centimeter) with a pad of cheesecloth using light pressure and a circular polishing motion for about 30 seconds. This procedure cleaned, activated and treated the glass. The test panels were then buffed dry with a piece of clean, dry cheesecloth and conditioned for about 20 minutes at about 23° C. and then were tested for the durability of the hydrophilic treatment. A blank test panel (i.e., one having been cleaned but not made hydrophilic) was used as a control. The control panel was cleaned with a water slurry of "Imsil" A-25 amorphous silica (from Illinois Mineral Company) and rinsed with deionized water. Durability of the hydrophilic treatments was shown by the Dye Exchange Test and the Cyclic Wear Test. The absorbance of the rinse solution was determined both initially and after the treated surface had been subjected to the Cyclic Wear Test. The abrasive materials used in the treatment compositions and the results of the Test are set forth in Table 5.

TABLE 5

| EXAMPLE | ABRASIVE MATERIAL | ABSORBANCE OF EXCHANGED DYE AFTER CHALLENGES | | | | | | |
|---|---|---|---|---|---|---|---|---|
| | | INITIAL | 10 CYCLES | 25 CYCLES | 50 CYCLES | 100 CYCLES | 250 CYCLES | 500 CYCLES |
| 60 | I | .75 | .54 | .50 | .49 | .42 | .48 | .47 |
| 61 | II | .82 | .55 | .51 | .45 | .43 | .42 | .43 |
| 62 | III | .82 | .59 | .56 | .55 | .52 | .51 | .44 |
| 63 | IV | 1.03 | .64 | .63 | .51 | .49 | .48 | .46 |
| 64 | Control | .36 | .36 | .42 | .44 | .42 | .36 | .36 |

I. Imsil A-10 amorphous silica (99% by weight less than 10 μm in size, available from Illinois Minerals Company)
II. Insil A-15 amorphous silica (99% by weight less than 15 μm in size, available from Illinois Minerals Company)
III. Imsil A-25 amorphous silica (99.9% by weight pass through a 400 mesh screen, available from Illinois Minerals Company)
IV. α-Quartz Imsil extracted from Ajax ®Brand household cleanser.

As can be seen from this data, a significant amount of the hydrophilic layer is present on the treated surfaces even after 500 cycles in the Cyclic Wear Test. This demonstrates the durability of the hydrophilic layer.

A Reliance ® All-Surface Writer, White No. 3366 was used to make a wax mark on each of the glass panels after 500 abrasion cycles. The mark was easily removed from the treated panels with a stream of water from a wash bottle and gentle rubbing. However, the control panel required rinsing and vigorous rubbing in order to remove the mark.

EXAMPLES 65–67

Separate sections of single strength window glass (7.6 cm by 7.6 cm) were rendered hydrophilic. The section employed in Example 65 was cleaned and activated as described in Examples 10–21 after which the organosilanol-sulfonic acid treatment solution of Example 2 was applied thereto. The sections employed in Examples 66–67 (duplicate examples) were cleaned, activated and made hydrophilic by a one-part cleaner-treatment composition which comprised 2% by weight of the organosilanol-sulfonic acid of Example 2, 10% by weight of Imsil A-10 abrasive material, 4% by weight of "Veegum HV" thickener (a magnesium aluminum silicate available from R. T. Vanderbilt Company) and 84% by weight of diluent (74% water and 10% ethylalcohol).

The treated slides were conditioned at 23° C. for 15 minutes and then subjected to the Dye Exchange Test and Spreading Water Drop Test both initially (i.e., before normalization of the surface) and finally after normalization of the treated surface with the chromic-sulfuric acid treatment described previously. The results of the tests are given in Table 6.

TABLE 6

| | ABSORBANCE | | | SPREADING WATER DROP | |
|---|---|---|---|---|---|
| EX-AMPLE | IN-ITIAL | FINAL* | RATIO INITIAL/FINAL* | IN-ITIAL (mm²) | FINAL* (mm²) |
| 65 | 0.64 | 0.23 | 2.78 | 18.1 | 6.6 |
| 66 | 0.48 | 0.20 | 2.40 | 13.2 | 4.9 |

TABLE 6-continued

| | ABSORBANCE | | | SPREADING WATER DROP | |
|---|---|---|---|---|---|
| EX-AMPLE | IN-ITIAL | FINAL* | RATIO INITIAL/FINAL* | IN-ITIAL (mm²) | FINAL* (mm²) |
| 67 | 0.38 | 0.22 | 1.73 | 13.2 | 4.9 |

*FINAL = Normalized

EXAMPLES 68–70

Three compositions were prepared. One composition (Example 68) was a one-part cleaner-treatment composition according to the invention. The other two compositions (Examples 69–70) were surfactant compositions (i.e., they contained no sulfonato-silanol). Each composition was applied to separate test panels of single strength window glass with a cheesecloth pad using light pressure and a circular polishing pattern for about 30 seconds. The panels were then buffed dry with a clean, dry pad of cheesecloth and conditioned for 20 minutes at about 23° C. The compositions (in parts by weight) employed in these Examples are set forth in Table 7.

TABLE 7

| FORMULATION | 68 | 69 | 70 |
|---|---|---|---|
| Organosilanol-sulfonic acid of Example 2 | 2 | — | — |
| Imsil A-25 | 10 | 10 | — |
| "Keltrol" | 1 | 1 | — |
| 2-propanol | 5 | 5 | — |
| Water (Deionized) | 82 | 82 | 98 |
| "Siponate DS-10" (Sodium dodecylbenzenesulfonate, available from Alcolac, Incorporated) | — | 2 | 2 |

After conditioning, the test panels were subject to a 500 Cycle Cyclic Wear Test. A Reliance ® All-Surface Writer, White No. 3366 was then used to make a wax mark on each of the test panels. The mark was easily removed from the panel of Example 68 with a stream of water from a wash bottle and gentle rubbing. However, the panels of Examples 69 and 70 required rinsing and vigorous rubbing in order to remove the marks.

EXAMPLES 71–73

One part cleaner-treatment compositions according to the invention were prepared and applied to separate test panels of single strength window glass. The panels were then buffed and conditioned as described in Examples 68–70. Durability of the hydrophilic treatments was demonstrated by the Spreading Water Drop Test. An initial determination (i.e., before challenge) and a determination after various numbers of challenges was made. The challenges were performed in accordance with the Cyclic Wear Test. The formulations (in parts by weight) employed and the results obtained from the "Spreading Water Drop" Test are set forth in Table 8.

TABLE 8

| FORMULATION | 71 | 72 | 73 |
|---|---|---|---|
| Organosilanol-sulfonic acid of Example 2 | 2 | 2 | 2 |
| Imsil A-25 | 10 | 10 | 10 |
| Keltrol | 1 | 1 | 1 |
| Siponate DS-10 | 0.2 | 2 | 5 |
| 2-propanol | 5 | 5 | 5 |
| Deionized Water | 81.8 | 81 | 77 |
| Spreading Water Drop* (Area in mm$^2$) | | | |
| Initial (0 cycles) | 13.4 | 14.7 | 20.6 |
| 10 Cycles | 13.4 | 16.1 | 16.1 |
| 25 Cycles | 13.4 | 18.3 | 16.1 |
| 100 Cycles | 13.4 | 15.4 | 14.0 |
| 500 Cycles | 10.3 | 13.4 | 14.7 |

*A cleaned but untreated glass panel had a "Spreading Water Drop" Test of about 8 mm$^2$.

A Reliance® All-Surface Writer, White No. 3366 was used to make a wax mark on each of the glass panels after 500 cycles. The mark was easily removed from the panels with a stream of water from a wash bottle.

EXAMPLE 74

A silicon monoxide primer coating was deposited on a polyester (i.e., poly(ethyleneterephthalate) film. The film was coated in a conventional vapor coating bell jar using a vacuum of $10^{-3}$ to $10^{-4}$ Torr. A liquid nitrogen trap was interposed between the vacuum pump and the bell jar to substantially eliminate back diffusion of organic vapors into the bell jar. Chunks of silicon monoxide (i.e., —SiO$_x$— where x is $\geq 1 < 2$, available commercially as Kemet® from Union Carbide Corporation) were placed in a crucible and heated to 1400°–1700° C. in the bell jar under vacuum (below $10^{-3}$ Torr) so that the vaporized silicon monoxide condensed on the surface of the polyester at a rate of 0.5 to 2.5 nanometers per second (nm/sec). The thickness of the coating was subsequently estimated to be 50 nm thick by use of an Inficon Crystal Deposition Detector. Two months later a clean pad (a Colitho® plate wipe) was used to apply a thin, visibly damp film of a treatment solution containing 3% by weight of the organosilanosulfonic acid of Example 2, 0.3% by weight sodium dodecylbenzenesulfonate and 96.7% by weight waterethanol (4:1 by volume) to the silicon monoxide coated polyester sheet (7.62 cm×7.62 cm). The hydrophilic film was conditioned at 23° C. for three hours. The surface was subsequently scrubbed three strokes with a wet Colitho® plate wipe followed by drying with a dry Colitho® plate wipe. The Spreading Water Drop area was determined to be 18 mm$^2$. A dye absorbance of 1.39 was measured by the Cationic Dye Exchange Test on a 7.6 cm by 7.6 cm section. The dye absorbance of an untreated silicon monoxide vapor coated polyester sheet of the same size was 0.14. The treated sheet released wax pencil markings from a Reliance® All-Surface Writer, White No. 3366) and skin oil with simple water rinsing. Additionally, the treated sheet could be rendered reversibly hydrophilic and hydrophobic as described in Example 27.

EXAMPLES 75-94

Additional substrates were primed with silicon monoxide and rendered durably hydrophilic as described in Example 74 except that the time elapsed between vapor coating and hydrophilic treatment varied from 5 minutes to two days, thereby indicating that the silicon monoxide coated substrates remained sufficiently activated over an extended period of time. The estimated thickness of the silicon monoxide layer and the results of the Spreading Water Drop Test are set forth in Table 9.

TABLE 9

| EXAMPLE | POLYMER | —(SiO$_x$)— Thickness (nm) | Spreading Water Drop Test Area (mm$^2$) |
|---|---|---|---|
| 75 | Plexiglas®[1] | 25 | 18.1 |
| 76 | Polycast®[2] | 25 | 18.1 |
| 77 | Polycarbonate[3] | 25 | 18.1 |
| 78 | Polyvinylchloride | 25 | 18.1 |
| 79 | Polyvinylfluoride | 25 | 15.2 |
| 80 | Polyvinylidenefluoride | 15 | 15.2 |
| 81 | Teflon[4] | 15 | 15.2 |
| 82 | Kapton®[5] | 25 | 18.1 |
| 83 | Phenol-formaldehyde resin | 25 | 12.3 |
| 84 | Polyethylene | 15 | 13.2 |
| 85 | Mica | 15 | 15.2 to 18.1 |
| 86 | Polycarbonate[3] | 5.8 | 12.3 |
| 87 | Acrylonitrile/butadiene/styrene copolymer | 6.5 | 13.2 |
| 88 | Formica®[6] | 6.5 | 15.2 |
| 89 | Aluminum Foil | 6.5 | 15.2 |
| 90 | Nylon | 6.5 | 9.1 to 13.2 |
| 91 | Polystyrene | 12 | 12.3 |
| 92 | Cellulose Acetate Butyrate | 12 | 12.3 |
| 93 | Polypropylene | 12 | 15.2 |
| 94 | Scotchlite®[7] No. 3270 | 6.5 | 12.3 |

[1]Poly-methylmethacrylate commerically available from Rohm & Haas Company.
[2]Poly-methylmethacrylate commerically available from Polycast Technology Corporation.
[3]Poly-methylmethacrylate commerically available from Rowland Company.
[4]Polytetrafluoroethylene, commerically available from E. I. duPont de Nemours and Company.
[5]Polyimide commerically available from E. I. du Pont de Nemours and Company.
[6]Melamine resin commericallly available from Formica Corporation.
[7]Reflective sheeting commerically avaliable from Minnesota Mining and Manufacturing Company.

The Spreading Water Drop test demonstrates that the treated surfaces were hydrophilic. This hydrophilicity was further demonstrated by making a wax pencil mark on each of the surfaces with a Reliance® All-Surface Writer, White No. 3366. The wax mark was readily removed from each of the surfaces by simply rinsing the surfaces with a stream of water from a wash bottle.

EXAMPLE 95-98

Various siliceous surfaces were cleaned, activated, treated, and conditioned using the composition and procedures of Example 23. The substrates treated and the results obtained are given in Table 10.

TABLE 10

| Example | Surface | Results |
|---|---|---|
| 95 | Glass Slide | Antifogging and easily released grease for over one year with gentle water washing. |
| 96 | Indoor Window Glass | Easily cleaned after one year by wiping with wet towel despite not having |

TABLE 10-continued

| Example | Surface | Results |
|---|---|---|
| | | been otherwise cleaned. An uncleaned section of glass required considerable effort in order to clean. |
| 97 | Eyeglasses | Provided antifogging properties for two to four weeks during winter months. |
| 98 | Exterior Auto Windshield | Improved visibility during rainfall on treated portion. Improved cleanability by low friction action of windshield wipers. |

EXAMPLE 99

A portion of a 7.5 cm×7.5 cm panel of single-strength window glass was cleaned, activated, treated and conditioned using the composition and procedures described in Example 23. Both the treated portion and the untreated portion of the glass panel was deliberately contaminated in separate areas by the following synthetic and natural greases and fluids:

| | |
|---|---|
| Silicone Stopcock Grease | (Dow Corning Co.) |
| Apiezon T Vacuum Grease | (Associated Electrical Industries, Ltd.) |
| Santovac 5 (a polyphenyl ether fluid) | (Monsanto Corp.) |
| FS Fluorosilsicone Grease | (Dow Corning Co.) |
| Aroclor 1242 (a chlorinated byphenyl fluid) | (Monsanto Corp.) |
| Fomblin-SH Fluorinated Fluid | (available from Penisular Chemical Co.) |
| Kel-F No. 90 Grease (a chlorotrifluoroethylene polymer) | (Minnesota Mining and Manufacturing Company) |
| Bis(2-ethyl hexyl)adipate (a diffusion pump fluid) | |
| Linseed oil, peanut oil, olive oil, cottonseed oil, and neatsfoot oil. | |

Without exception, these substances were quickly released from the treated glass surface upon gentle rinsing with a thin stream of tepid tap water. There was no trace of contamination upon drying the rinsed and treated area. However, the untreated portion remained grossly contaminated, and in most cases, the areas of contamination of said untreated portion increased upon similar rinsing.

EXAMPLE 100

A 7.5 cm by 7.5 cm panel of single-strength window glass was cleaned, activated, treated and conditioned using the composition and procedure described in Example 23. A portion of the treated surface was rinsed first with tap water and then ion exchanged by rinsing with about 1 ml. of a 1% by weight aqueous solution of the fluorinated quaternary ammonium salt, $C-C_8F_{17}SO_2NHCH_2CH_2CH_2N(CH_3)_3{}^+Cl^-$. It was then rinsed with deionized water. The exchanged surface became reversibly hydrophobic and additionally, exhibited reversible oleophobic behavior. Thus, when S.A.E. No. 10 lubricating oil was applied dropwise to the exchanged and unexchanged surface, it remained in nonspreading drops on the dried exchanged portion surface but slowly spread on the unexchanged portion. The oleophobic exchanged surface was connected directly to an oleophibic but hydrophobic surface by rinsing with 1% aqueous hexadecyltrimethylammonium chloride followed by deionized water rinsing.

EXAMPLE 101

A section of single-strength window glass was selectively cleaned, activated and rendered hydrophibic with the composition and according to the procedures of Example 23 so as to leave a portion of the glass untreated. The untreated section was surrounded by the treated section.

The treated portion of the glass was then selectively rendered oleophobic using the quaternary salt and method described in Example 100 so as to leave a portion thereof non-oleophobic. THe glass was then rinsed with deionized water leaving both the untreated area and the treated hydrophibic area (i.e., nonoleophobic area) surrounded by the oleophobic area.

S.A.E. No. 10 lubricating oil was dropped onto the untreated area and onto the treated hydrophilic area. The oil remained in said areas even though the panel was tilted and shaken. Additionally, the oleophobic area resisted the spread of drops of acetone which were placed thereon while the treated hydrophilic area permitted the spread of drops of acetone placed thereon.

What is claimed is:

1. An aqueous solution comprising a sulfonato-organosilanol compound having at least one sulfonato-organic substituent, wherein the weight percentage of oxygen in said compound is at least about 30%, and the weight percentage of silicon in said compound is not greater than about 15%, said percentages being taken with reference to the water-free acid form of said compound.

2. A solution in accordance with claim 1 wherein said sulfonato-organosilanol compound has the formula

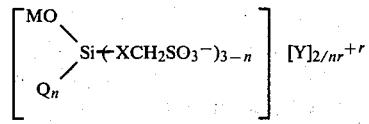

wherein

Q is selected from hydroxyl, alkyl groups containing from 1 to about 4 carbon atoms and alkoxy groups containing from 1 to about 4 carbon atoms;

M is selected from hydrogen, alkali metals and organic cations of strong organic bases having a number average molecular weight of less than about 150 and a $pK_a$ of greater than about 11;

X is an organic linking group;

Y is selected from hydrogen, alkaline earth metals, cations of protonated weak bases having an average molecular weight of less than about 200 and a $pK_a$ of less than about 11, alkali metals and organic cations of strong organic bases having an average molecular weight of less than about 150 and a $pK_a$ of greater than about 11, provided that M is hydrogen when Y is selected from hydrogen, alkaline earth metals and organic cations of said protonated weak base;

r is equal to the valence of Y; and n is 1 or 2.

3. A solution in accordance with claim 2 wherein X is selected from alkylene groups, cycloalkylene groups, alkyl-substituted cycloalkylene groups, hydroxy-substituted alkylene groups, hydroxy-substituted mono-oxa alkylene groups, divalent hydrocarbon groups having mono-oxa backbone substitution, divalent hydrocarbon groups having mono-thia backbone substitution, divalent hydrocarbon groups having monooxo-thia backbone substitution, divalent hydrocarbon groups having dioxo-thia backbone substitution, arylene groups, arylalkylene groups, alkylarylene groups and substitutied alkylarylene groups.

4. A solution in accordance with claim 3 wherein X is selected from alkylene groups, hydroxy-substituted alkylene groups and hydroxy-substituted mono-oxa alkylene groups.

5. A solution in accordance with claim 2 wherein said sulfonato-organosilanol compound comprises an organosilanol-sulfonic acid of the formula

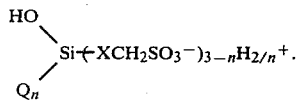

6. A solution in accordance with claim 5 having a pH of less than about 5.

7. A solution in accordance with claim 5 wherein said organosilanol-sulfonic acid has the formula $(HO)_3$-$SiXCH_2SO_3^-H^+$.

8. A solution in accordance with claim 7, wherein X is $-(CH_2)_m-$, where m is an integer of from 1 to about 8.

9. A solution in accordance with claim 8 wherein m is 1.

10. A solution in accordance with claim 8 wherein m is 2.

11. A solution in accordance with claim 7 wherein X is

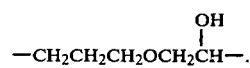

12. A solution in accordance with claim 5 wherein said organosilanol-sulfonic acid has the formula

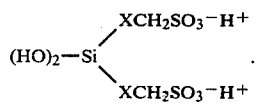

13. A solution in accordance with claim 12 wherein X is $-CH_2-$.

14. A solution in accordance with claim 5 wherein said organosilanol-sulfonic acid has the formula

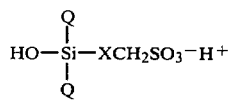

wherein Q is an alkyl group containing from 1 to about 4 carbon atoms.

15. A solution in accordance with claim 2 wherein said sulfonato-organosilanol compound comprises an organosilanolate-sulfonic acid salt wherein M and Y are each selected from alkali metals and organic cations of strong organic bases having an average molecular weight of less than about 150 and a $pK_a$ of greater than about 11.

16. A solution in accordance with claim 15 having a pH greater than about 9.

17. A solution in accordance with claim 15 wherein Q is selected from hydroxyl, alkyl groups containing from 1 to about 4 carbon atoms and alkoxy groups containing from 1 to about 4 carbon atoms, provided that at least one of said Q groups is hydroxyl.

18. A solution in accordance with claim 15, wherein n is 2 and r is 1.

19. A solution in accordance with claim 2 wherein said sulfonato-organosilanol compound comprises an organosilanol-sulfonic acid salt wherein M is hydrogen; Q is selected from hydroxyl and alkyl groups of from 1 to about 4 carbon atoms and Y is selected from alkaline earth metals, cations of protonated weak bases having an average molecular weight of less than about 200 and a pKa of less than about 11, alkali metals and cations of strong organic bases having an average molecular weight of less than about 150 and a pKa of greater than about 11.

20. A solution in accordance with claim 19 having a pH in the range of about 5 to 9.

21. A solution in accordance with claim 19, wherein Q is hydroxyl.

22. A solution in accordance with claim 21, wherein n is 2 and r is 1.

23. A solution in accordance with claim 21 wherein n and r are each 1.

24. A solution in accordance with claim 1 further comprising a surfactant.

25. An organosilanol sulfonic acid having the formula

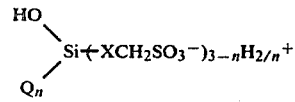

wherein Q is selected from hydroxyl, alkyl groups containing from 1 to about 4 carbon atoms and alkoxy groups containing from 1 to about 4 carbon atoms; X is an organic linking group; and n is 1 or 2; wherein the weight percentage of oxygen in said compound is at least about 30%, and the weight percentage of silicon in said compound is not greater than about 15%; said percentages being taken with respect to the water-free acid form of said compound.

26. An organosilanol-sulfonic acid in accordance with claim 25 wherein X is selected from alkylene groups, cycloalkylene groups, alkyl-substituted cycloalkylene groups, hydroxy-substituted alkylene groups, hydroxy-substituted mono-oxa alkylene groups, divalent hydrocarbon groups having mono-oxa backbone substitution, divalent hydrocarbon groups having mono-thia backbone substitution, divalent hydrocarbon groups having mono-oxa thia backbone substitution, divalent hydrocarbon groups having dioxo-thia backbone substitution, arylene groups, arylalkylene groups, alkylarylene groups, and substituted alkylarylene groups.

27. An organosilanol-sulfonic acid in accordance with claim 26 wherein X is selected from alkylene groups, hydroxy-substituted alkylene groups and hydroxy-substituted mono-oxa alkylene groups.

28. An organosilanol-sulfonic acid in accordance with claim 25 having the formula $(HO)_3Si-X-CH_2SO_3^-H^+$.

29. An organosilanol sulfonic acid in accordance with claim 28 wherein X is $-(CH_2)_m-$, where m is an integer of from 1 to about 8.

30. An organosilanol sulfonic acid in accordance with claim 29 wherein m is 1.

31. An organosilanol sulfonic acid in accordance with claim 29 wherein m is 2.

32. An organosilanol sulfonic acid in accordance with claim 27 wherein X is

33. An organosilanol sulfonic acid in accordance with claim 25 having the formula

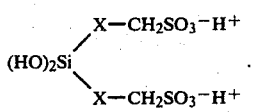

34. An organosilanol-sulfonic acid in accordance with claim 33 wherein X is $-CH_2-$.

35. An organosilanolate-sulfonic acid salt having the formula

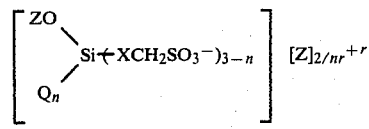

wherein Q is selected from hydroxyl, alkyl groups containing from 1 to about 4 carbon atoms and alkoxy groups containing from 1 to about 4 carbon atoms; Z is selected from alkali metals and cations of strong organic bases having an average molecular weight of less than about 150 and a $pK_a$ of greater than about 11; r is equal to the valence of Z; and n is an integer of 1 or 2; wherein the weight percentage of oxygen in said compound is at least about 30%; and the weight percentage of silicon in said compound is not greater than about 15%, said percentages being taken with respect to the water-free acid form of said compound.

36. An organosilanolate-sulfonic acid salt in accordance with claim 35 wherein Z is selected from sodium, potassium, $(CH_3)_4N^+$, and $(CH_3CH_2)_4N^+$.

37. An organosilanolate-sulfonic acid salt in accordance with claim 35 wherein n is 2 and r is 1.

38. An organosilanolate-sulfonic acid salt in accordance with claim 35, wherein n is 1 and r is 1.

* * * * *